United States Patent
Li

(10) Patent No.: US 9,788,975 B2
(45) Date of Patent: Oct. 17, 2017

(54) METHOD OF ESTIMATING SOFT TISSUE BALANCE FOR KNEE ARTHROPLASTY

(75) Inventor: Jia Li, Warsaw, IN (US)

(73) Assignee: ZIMMER, INC., Fort Wayne, IN (US)

( * ) Notice: Subject to any disclaimer, the term of this patent is extended or adjusted under 35 U.S.C. 154(b) by 80 days.

(21) Appl. No.: 13/283,879

(22) Filed: Oct. 28, 2011

(65) Prior Publication Data

US 2013/0110250 A1    May 2, 2013

(51) Int. Cl.
| | | |
|---|---|---|
| A61B 17/15 | (2006.01) | |
| A61F 2/46 | (2006.01) | |
| A61B 34/10 | (2016.01) | |
| B33Y 80/00 | (2015.01) | |
| A61B 5/107 | (2006.01) | |

(52) U.S. Cl.
CPC .......... *A61F 2/4657* (2013.01); *A61B 5/1075* (2013.01); *A61B 34/10* (2016.02); *A61B 5/1071* (2013.01); *A61B 17/155* (2013.01); *A61B 17/157* (2013.01); *A61B 2034/105* (2016.02); *A61B 2034/108* (2016.02); *A61F 2002/4666* (2013.01); *B33Y 80/00* (2014.12)

(58) Field of Classification Search
USPC .......... 606/80, 87–88, 96–98, 86 R
See application file for complete search history.

(56) References Cited

U.S. PATENT DOCUMENTS

2007/0276224 A1* 11/2007 Lang et al. ............ 600/410
2011/0029093 A1*  2/2011 Bojarski .............. A61F 2/389
                                                  623/20.35

OTHER PUBLICATIONS

"A quantitative method of effective soft tissue management for varus knee in total knee replacement surgery using navigational techniques" F. Picard et al., Proceedings of the Institution of Mechanical Engineers, vol. 221 Part H, 2007.
"Evaluation of soft-tissue balance during total knee arthroplasty" Hideyuki Sasanuma et al., Journal of Orthopaedic Surgery, vol. 18, No. 1, Apr. 2010, pp. 26-3.
"Comparison of total knee arthroplasty using computer-assisted navigation versus conventional guiding systems: a prospective study" CH Pang et al., Journal of Orthopaedic Surgery, vol. 17, No. 2, Aug. 2009, pp. 170-173.

* cited by examiner

*Primary Examiner* — Samuel Hanna
(74) *Attorney, Agent, or Firm* — Norton Rose Fulbright Canada LLP

(57) ABSTRACT

A method is provided for evaluating the tension or laxity of the soft tissue surrounding a patient's knee joint. Based on this evaluation, a surgeon may determine a desired resection depth for a knee arthroplasty procedure that will achieve an appropriate spacing between adjacent, articulating components of the knee joint.

15 Claims, 10 Drawing Sheets

METHOD OF ESTIMATING SOFT TISSUE BALANCE FOR KNEE ARTHROPLASTY

FIELD OF THE DISCLOSURE

The present disclosure relates to knee arthroplasty procedures. More particularly, the present disclosure relates to a method for evaluating soft tissue during knee arthroplasty procedures.

BACKGROUND OF THE DISCLOSURE

In a natural knee joint, the distal end of the femur articulates against the proximal end of the tibia. If the natural knee joint becomes diseased or damaged, a knee arthroplasty procedure may be performed to repair the distal end of the femur and/or the proximal end of the tibia. The knee arthroplasty procedure involves resecting the distal end of the femur and/or the proximal end of the tibia and replacing the resected bones with prosthetic components that are designed to replicate articulation of the natural knee joint.

SUMMARY

The present disclosure provides a method for evaluating the tension or laxity of the soft tissue surrounding a patient's knee joint. Based on this evaluation, a surgeon may determine a desired resection depth for a knee arthroplasty procedure that will achieve an appropriate spacing between adjacent, articulating components of the knee joint.

According to an embodiment of the present disclosure, a method is provided for performing an arthroplasty procedure on a patient's knee joint. The knee joint includes a femur, a tibia, and soft tissue. The method includes the steps of: comparing a first image of the knee joint in an unloaded state and a second image of the knee joint in a loaded state; evaluating at least one movement of the knee joint between the first and second images to evaluate laxity of the knee joint; and resecting at least one of the femur and the tibia to a desired resection depth based on the at least one movement evaluated during the evaluating step.

According to another embodiment of the present disclosure, a method is provided for performing an arthroplasty procedure on a patient's knee joint. The knee joint includes a femur, a tibia, and soft tissue. The method includes the steps of: measuring at least one movement of the knee joint between an unloaded state and a loaded state; and resecting at least one of the femur and the tibia to a desired resection depth based on the at least one movement measured during the measuring step.

According to yet another embodiment of the present disclosure, a method is provided for performing an arthroplasty procedure on a patient's knee joint. The knee joint includes a femur, a tibia, and soft tissue. The method includes the steps of: capturing a first image of the knee joint in an unloaded state; capturing a second image of the knee joint in a loaded state; aligning at least one corresponding anatomic feature of the first and second images; measuring at least one movement of the knee joint between the first and second images to evaluate laxity of the knee joint; and determining a desired resection depth of at least one of the femur and the tibia based on the measuring step.

BRIEF DESCRIPTION OF THE DRAWINGS

The above-mentioned and other features and advantages of this disclosure, and the manner of attaining them, will become more apparent and the invention itself will be better understood by reference to the following description of embodiments of the invention taken in conjunction with the accompanying drawings, wherein.

Corresponding reference characters indicate corresponding parts throughout the several views. The exemplifications set out herein illustrate exemplary embodiments of the invention and such exemplifications are not to be construed as limiting the scope of the invention in any manner.

DETAILED DESCRIPTION

Figure 1:
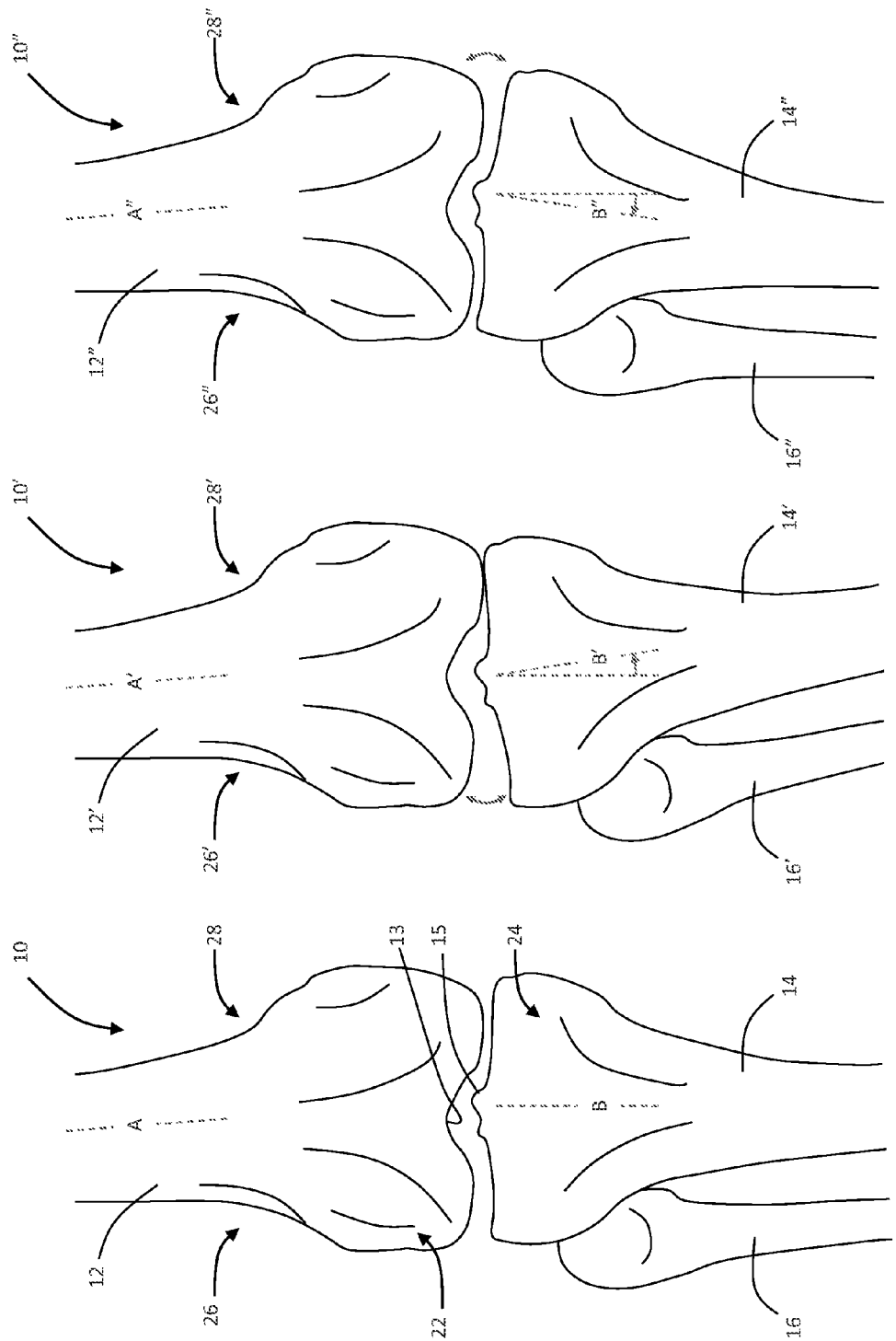
FIG. 1A is an anterior elevational view of a patient's knee joint shown in a normal, aligned state, the knee joint including a femur and a tibia.
FIG. 1B is another anterior elevational view of the patient's knee joint shown in a varus state.
FIG. 1C is another anterior elevational view of the patient's knee joint shown in a valgus state.

A patient's knee joint 10 is depicted in FIG. 1A. Knee joint 10 is formed between the patient's femur 12 and tibia 14. Specifically, knee joint 10 is formed between distal end 22 of the patient's femur 12 and proximal end 24 of the patient's tibia 14. The patient's patella is not shown in FIG. 1A, but the patient's fibula 16 is shown in FIG. 1A to distinguish lateral side 26 from medial side 28 of knee joint 10.

As shown in FIG. 1A, femur 12 extends along anatomic axis A and includes an intercondylar notch or recess 13. Tibia 14 extends along anatomic axis B and includes a tibial eminence 15. During normal articulation of knee joint 10, distal end 22 of the patient's femur 12 rolls back and forth across proximal end 24 of the patient's tibia 14, with a tibial eminence 15 extending proximally from tibia 14 and into intercondylar recess 13 of femur 12.

The bones of knee joint 10 are surrounded by soft tissue to support and stabilize knee joint 10. The soft tissue of knee joint 10 includes various ligaments (not shown) extending between femur 12 and tibia 14, such as the lateral collateral ligament (LCL), which stabilizes lateral side 26 of knee joint 10, the medial collateral ligament (MCL), which stabilizes medial side 28 of knee joint 10, the anterior cruciate ligament (ACL), which limits rotation and the forward movement of tibia 14, and the posterior cruciate ligament (PCL), which limits backward movement of tibia 14. The soft tissue of knee joint 10 also includes various tendons and muscles (not shown).

The alignment of the patient's knee joint 10, and more specifically the alignment between anatomic axis A of the patient's femur 12 and anatomic axis B of the patient's tibia 14, may vary. Knee joint 10 is shown in a normal state in FIG. 1A, in a varus state in FIG. 1B, and in a valgus state in FIG. 1C.

In the normal state of FIG. 1A, anatomic axis A of femur 12 extends slightly laterally relative to anatomic axis B of tibia 14. For example, anatomic axis A of femur 12 may extend 5 degrees, 6 degrees, or 7 degrees laterally relative to anatomic axis B of tibia 14. Although anatomic axis A and anatomic axis B of knee joint 10 are not "aligned" (i.e., coaxial or parallel) in FIG. 1A, femur 12 and tibia 14 of knee joint 10 may be described as being "aligned" in FIG. 1A.

In the varus state of FIG. 1B, knee joint 10' appears to bow laterally outward, because anatomic axis B' of tibia 14' has rotated medially inward relative to anatomic axis A' of femur 12'. To offset this medially inward rotation, tibia 14' may also shift or translate laterally outward relative to femur 12'.

In the valgus state of FIG. 1C, knee joint 10" appears to bow medially inward, because anatomic axis B" of tibia 14" has rotated laterally outward relative to anatomic axis A" of femur 12". To offset this laterally outward rotation, tibia 14" may also shift or translate medially inward relative to femur 12".

One variable that may affect the alignment of knee joint 10 is the relative laxity or tension of the soft tissue surrounding knee joint 10. For example, knee joint 10 may be in the normal state of FIG. 1A when the soft tissue on lateral side 26 of knee joint 10 and the soft tissue on medial side 28 of knee joint 10 are balanced. Knee joint 10' may be in the varus state of FIG. 1B when the soft tissue on lateral side 26' of knee joint 10' is relatively lax and the soft tissue on medial side 28' of knee joint 10' is relatively tense. Knee joint 10" may be in the valgus state of FIG. 1C when the soft tissue on lateral side 26" of knee joint 10" is relatively tense and the soft tissue on medial side 28" of knee joint 10" is relatively lax.

Another variable that may affect the alignment of knee joint 10 is the force applied to knee joint 10. For example, knee joint 10 may be in the normal state of FIG. 1A when the patient is lying down in a supine position without subjecting knee joint 10 to a load. Knee joint 10' may be in the varus state of FIG. 1B when subjected to a laterally directed force. Knee joint 10" may be in the valgus state of FIG. 1C when subjected to a medially directed force.

These variables may also work in combination to affect the alignment of knee joint 10. For example, knee joint 10 may be in the normal state of FIG. 1A when the patient is lying down in a supine position without subjecting knee joint 10 to a load. However, when the patient is standing in an upright position and subjecting knee joint 10 to a load, the surrounding soft tissue may move knee joint 10 into the varus state of FIG. 1B or the valgus state of FIG. 1C. The more lax the surrounding soft tissue, the more knee joint 10 may move between the supine position and the upright position. By contrast, the more tense the surrounding soft tissue, the less knee joint 10 may move between the supine position and the upright position. In certain cases, the surrounding soft tissue may be so tight that the patient is unable to bend knee joint 10, a condition known as flexion contracture.

If knee joint 10 becomes diseased or damaged, a knee arthroplasty procedure may be performed to repair distal end 22 of the patient's femur 12 and/or proximal end 24 of the patient's tibia 14. The present disclosure provides a method 100 (FIG. 2) for estimating the laxity or tension of knee joint 10 during such a knee arthroplasty procedure. Method 100 is exemplified with reference to FIGS. 3-9.

Figure 2:
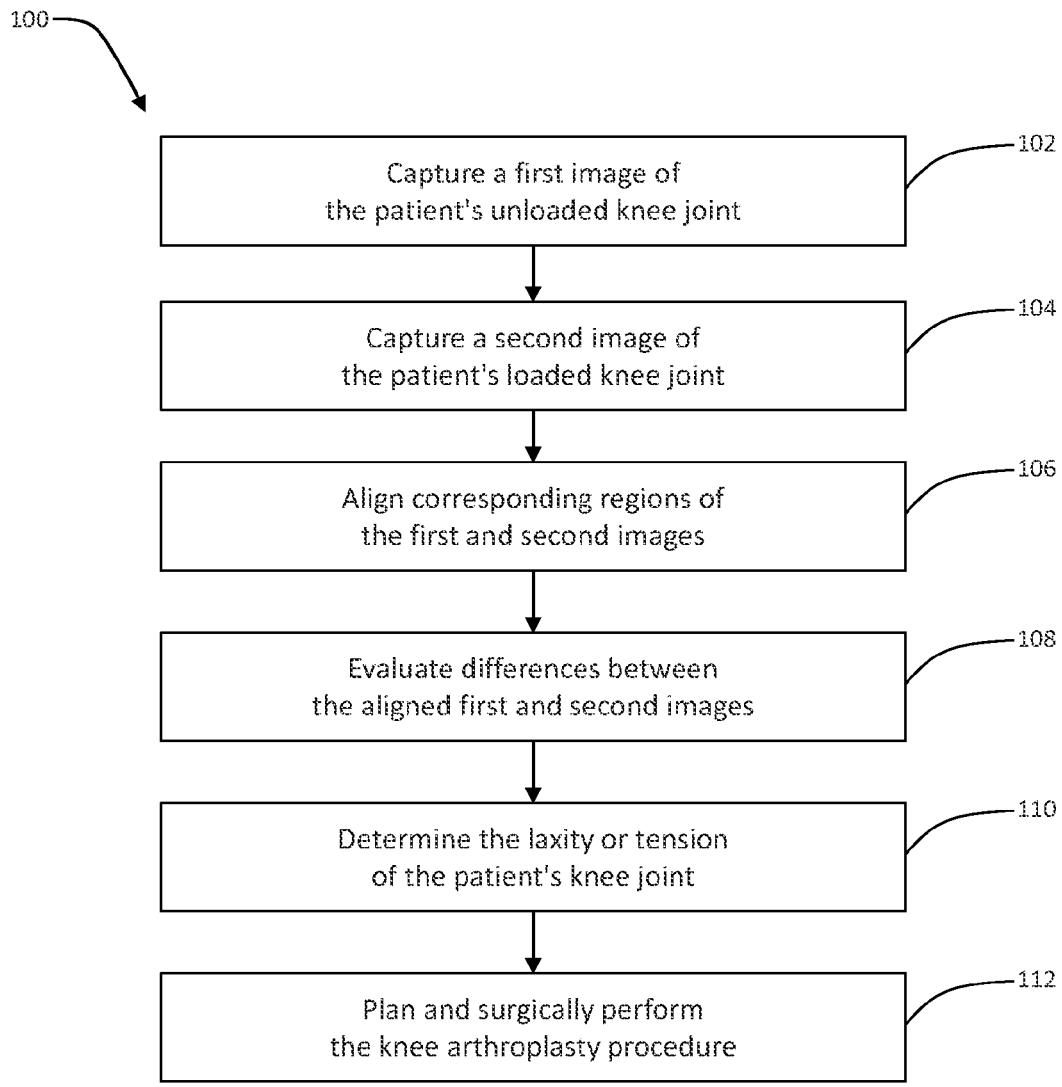
FIG. 2 is a flow chart of an exemplary method for performing a knee arthroplasty procedure.
Figure 3:
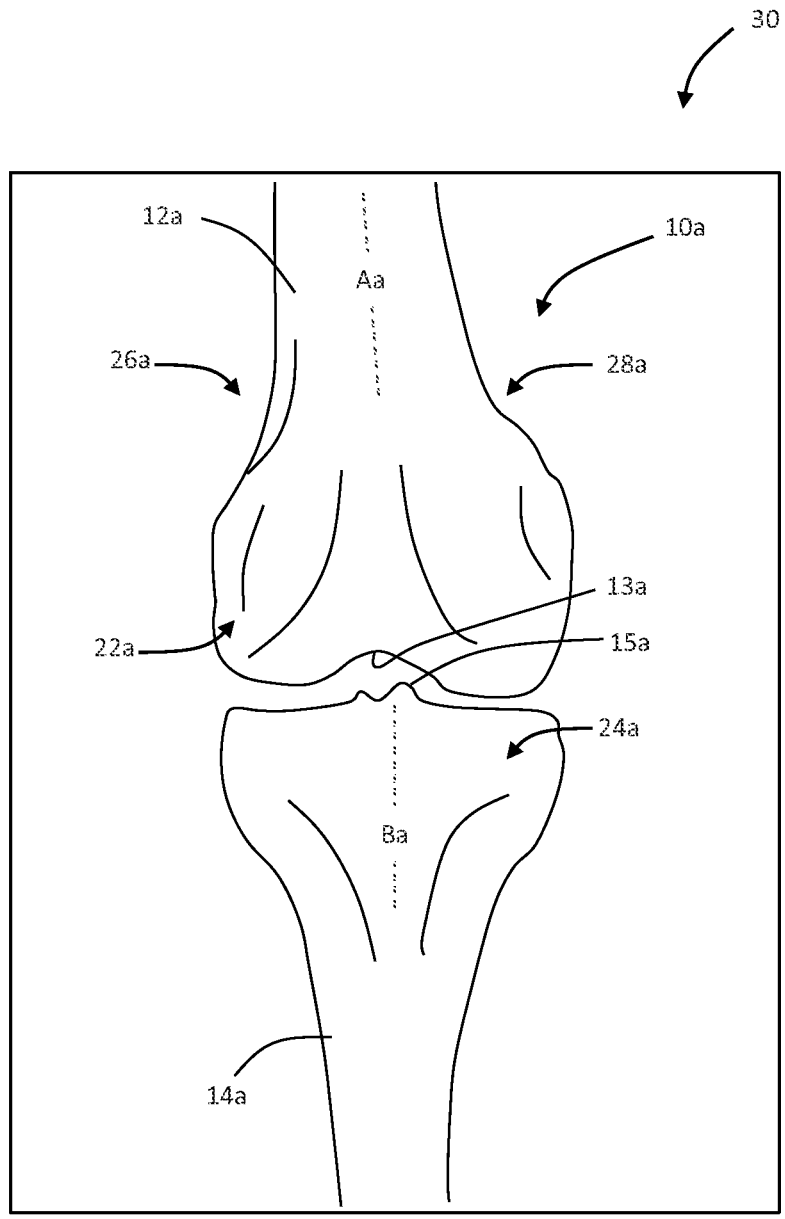
FIG. 3 is a plan view of a first image taken with the patient's knee joint in an unloaded state.

Beginning at step 102 of method 100 (FIG. 2), and as shown in FIG. 3, a surgeon or another party generates data representative of the patient's knee joint 10a in an unloaded state. This data may include a visual representation or image of the patient's knee joint 10a, which may be in the form of a two-dimensional image or a three-dimensional model, for example. Thus, step 102 may involve capturing at least one first image 30 of the patient's knee joint 10a in the unloaded state. To capture the unloaded knee joint 10a in the first image 30, the patient may be instructed to lie down in a supine position. The first image 30 may be captured using a suitable imaging modality, such as X-ray, fluoroscopy, magnetic resonance imaging (MRI), computed tomography (CT), or ultrasound, for example.

According to an exemplary embodiment of the present disclosure, the first image 30 is a digital, three-dimensional model of the patient's knee joint 10a. The first image 30 may be captured using a suitable three-dimensional imaging modality, such as MRI or CT. As discussed above, it is also within the scope of the present disclosure that the first image 30 is a two-dimensional image.

The first image 30 may be generated and processed using a suitable computer having, for example, image processing software and/or computer-aided design (CAD) software installed thereon. The computer may be programmed to digitally process, evaluate, and combine multiple images of the patient's knee joint 10a. For example, the computer may be programmed to combine a plurality of two-dimensional X-ray images to generate the digital, three-dimensional model. The computer may also be programmed to digitally segment, or differentiate, desired anatomic structures (e.g., bone tissue) from undesired structures (e.g., surrounding soft tissue) to create the first image 30. For example, the computer may be programmed to assign a grey value to each pixel of the image, set a threshold grey value, and segment desired pixels from undesired pixels based on the threshold grey value, as discussed in U.S. Pat. No. 5,768,134 to Swaelens et al., the disclosure of which is expressly incorporated herein by reference.

Using the first image 30, the surgeon may evaluate and identify certain features of femur 12a and tibia 14a. For example, the surgeon may use the first image 30 to evaluate the surface contour, size, and bone quality of femur 12a and tibia 14a. Also, the surgeon may use the first image 30 to identify features such as anatomic axis Aa of femur 12a, intercondylar recess 13a of femur 12a, anatomic axis Ba of tibia 14a, and eminence 15a of tibia 14a.

Figure 4:
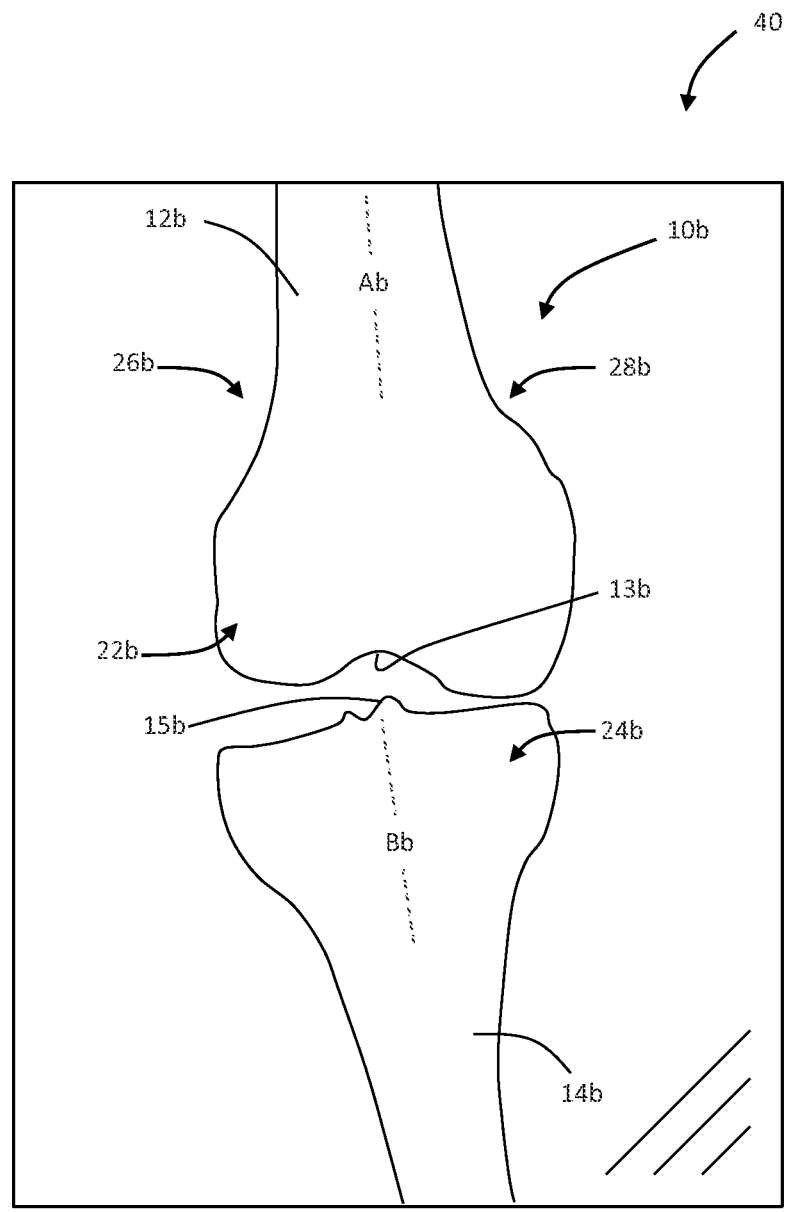
FIG. 4 is a plan view of a second image taken with the patient's knee joint in a loaded state.

Continuing to step 104 of method 100 (FIG. 2), and as shown in FIG. 4, the surgeon or another party generates data representative of the patient's knee joint 10b in a loaded state. This data may include a visual representation or image of the patient's knee joint 10b, which may be in the form of a two-dimensional image or a three-dimensional model, for example. Thus, step 104 may involve capturing at least one second image 40 of the patient's knee joint 10b in the loaded state. To capture the loaded knee joint 10b in the second image 40, the patient may be instructed to stand in an upright position, subjecting the loaded knee joint 10b of FIG. 4 to more force than the unloaded knee joint 10a of FIG. 3. For simplicity and efficiency, the second image 40 may be captured using a suitable two-dimensional imaging modality, such as X-ray. It is also within the scope of the present disclosure that the second image 40 may be captured using a three-dimensional imaging modality.

Using the second image 40, the surgeon may evaluate and identify certain features of femur 12b and tibia 14b. For example, the surgeon may use the second image 40 to identify features such as anatomic axis Ab of femur 12b, intercondylar recess 13b of femur 12b, anatomic axis Bb of tibia 14b, and eminence 15b of tibia 14b.

The first and second images 30, 40 shown and described herein are anterior views of the patient's knee joint 10a, 10b, respectively. It is also within the scope of the present disclosure to capture other views of the patient's knee joint 10a, 10b, including lateral, medial, and/or posterior views.

The unloaded knee joint 10a is shown in of FIG. 3 in a substantially normal or "aligned" state. Compared to the unloaded knee joint 10a of FIG. 3, the loaded knee joint 10b of FIG. 4 has transitioned into a more varus state. It is also within the scope of the present disclosure that another patient's knee joint may transition into a more valgus state when loaded (See FIG. 1C).

Figure 5:
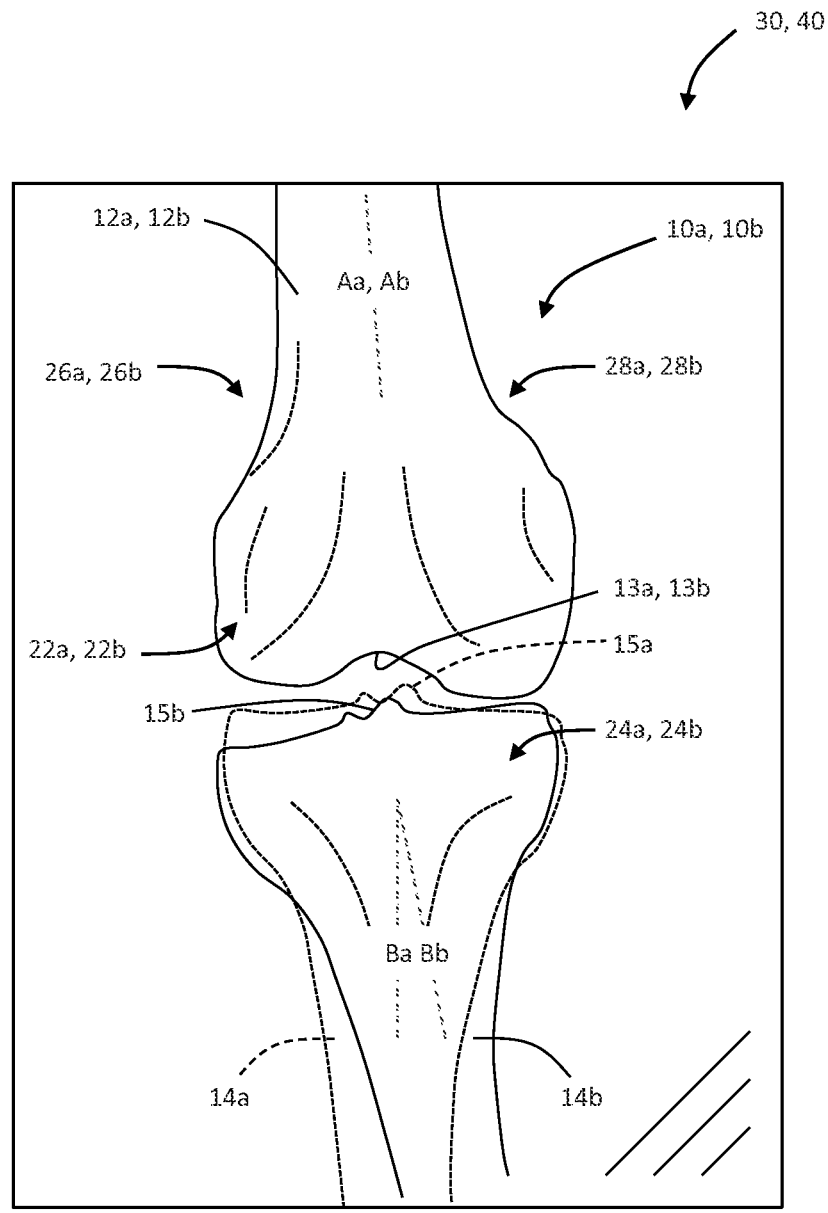
FIG. 5 is a plan view of the second image overlying the first image to align corresponding femoral regions of the first and second images.

In step 106 of method 100 (FIG. 2), and as shown in FIG. 5, corresponding regions of the first and second images 30, 40 are aligned. According to an exemplary embodiment of the present disclosure, the aligning step 106 of method 100 is performed using a suitable computer, which may be the same computer discussed above with respect to the capturing step 102. The computer may automatically align corresponding regions of the first and second images 30, 40 by performing best-fit calculations, for example. Alternatively, the computer may respond to manual instructions from the surgeon or another party to digitally align corresponding regions of the first and second images 30, 40. Rather than aligning the first and second images 30, 40 using the computer, it is also within the scope of the present disclosure that the surgeon or another party may align tangible, transparent versions of the first and second images 30, 40, for example.

The aligning step 106 may involve combining, mapping, or overlapping corresponding regions of the first and second images 30, 40, such as by overlaying the second image 40 onto the first image 30, or vice versa. As discussed above, at least one of the first and second images 30, 40 may be transparent to facilitate this overlaying step. In the illustrated embodiment of FIG. 5, for example, the second image 40 overlays the first image 30 to align corresponding regions of the femurs 12a, 12b, such as the corresponding anatomic axes Aa, Ab, the corresponding curved distal ends 22a, 22b (e.g., the corresponding intercondylar recesses 13a, 13b of the curved distal ends 22a, 22b), the corresponding elongate shafts, and/or other corresponding regions of the femurs 12a, 12b. If one or both of the first and second images 30, 40 are three-dimensional models, the first and second images 30, 40 may be aligned by generating and then aligning two-dimensional, planar projections of the three-dimensional models. The computer may generate such projections by performing linear algebraic calculations, for example.

Various techniques may be used to ensure that the first and second images 30, 40 are similar in scale during the aligning step 106. In one embodiment, the surgeon may apply magnification markers to the patient's bones when capturing the first and second images 30, 40. Then, the surgeon may reference the magnification markers to scale the first and second images 30, 40. In another embodiment, the surgeon may ensure that corresponding anatomic features captured in the first and second images 30, 40 are scaled to the same dimension. For example, the surgeon may ensure that the bones captured in the first and second images 30, 40 have the same overall width, the same overall length, the same epicondylar axis length, the same anatomic axis length, and/or other similar dimensions.

During the aligning step 106, it is within the scope of the present disclosure that the femurs 12a, 12b and the tibias 14a, 14b of the first and second images 30, 40 may not be perfectly aligned due to joint rotation between the unloaded, supine position and the loaded, standing position. Such rotation may be one factor in determining the laxity or tension of the patient's knee joint 10.

Next, during step 108 of method 100 (FIG. 2), the surgeon or another party evaluates differences between the aligned first and second images 30, 40. If the femurs 12a, 12b of the first and second images 30, 40 are aligned during step 106, for example, differences between the tibias 14a, 14b of the first and second images 30, 40 may be evaluated during step 108. Because the first image 30 captures the unloaded knee joint 10a with the patient lying down in a supine position and the second image 40 captures the loaded knee joint 10b with the patient standing upright, the evaluating step 108 allows the surgeon to evaluate the patient's loaded, standing knee joint 10b versus the patient's unloaded, supine knee joint 10a.

It is also within the scope of the present disclosure to align corresponding regions of the tibias 14a, 14b of the first and second images 30, 40 during the aligning step 106. In this case, differences between the femurs 12a, 12b of the first and second images 30, 40 would be evaluated during step 108.

It is further within the scope of the present disclosure to divide one of the images, such as the second image 40, into segments—one segment including the femur 12b and the other segment including the tibia 14b. Then, during the aligning step 106, the surgeon or another party would align both the femurs 12a, 12b and the tibias 14a, 14b of the first and second images 30, 40. In this case, differences between the divided segments of the second image 40 would be evaluated during step 108.

Figure 6A:
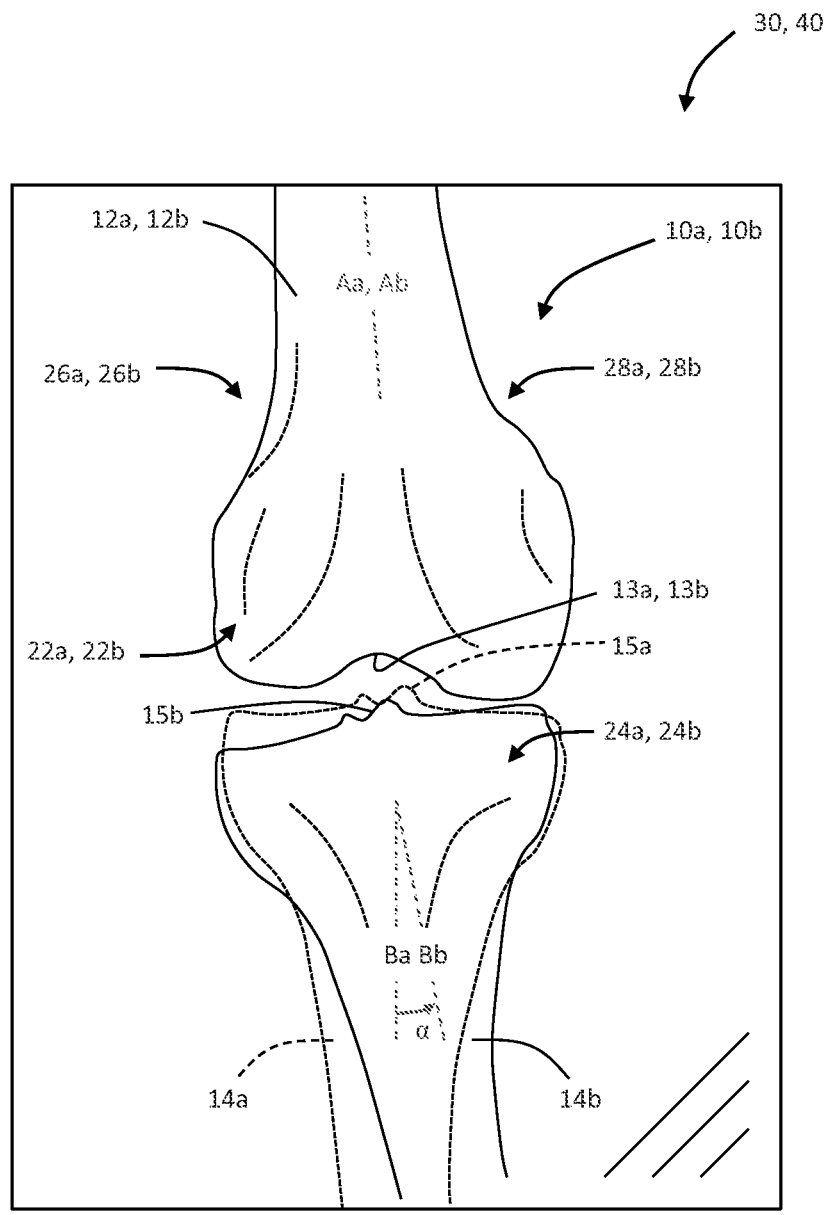
FIG. 6A is a plan view similar to FIG. 5 showing a first measurement of tibial movement between the first and second images.

As shown in FIG. 6A, the evaluating step 108 may involve measuring an angle α between the tibial anatomic axis Ba of the first image 30 and the tibial anatomic axis Bb of the second image 40. In this embodiment, angle α represents the degree of rotation between the patient's unloaded, supine knee joint 10a and the patient's loaded, standing knee joint 10b. In the illustrated embodiment of FIG. 6A, for example, the patient's knee joint becomes more varus when loaded, because anatomic axis Bb of tibia 14b has rotated medially inward by angle α relative to anatomic axis Ab of femur 12b. Angle α may be more easily measured when the first and second images 30, 40 depict the entire length of tibias 14a, 14b, respectively.

Figure 6B:
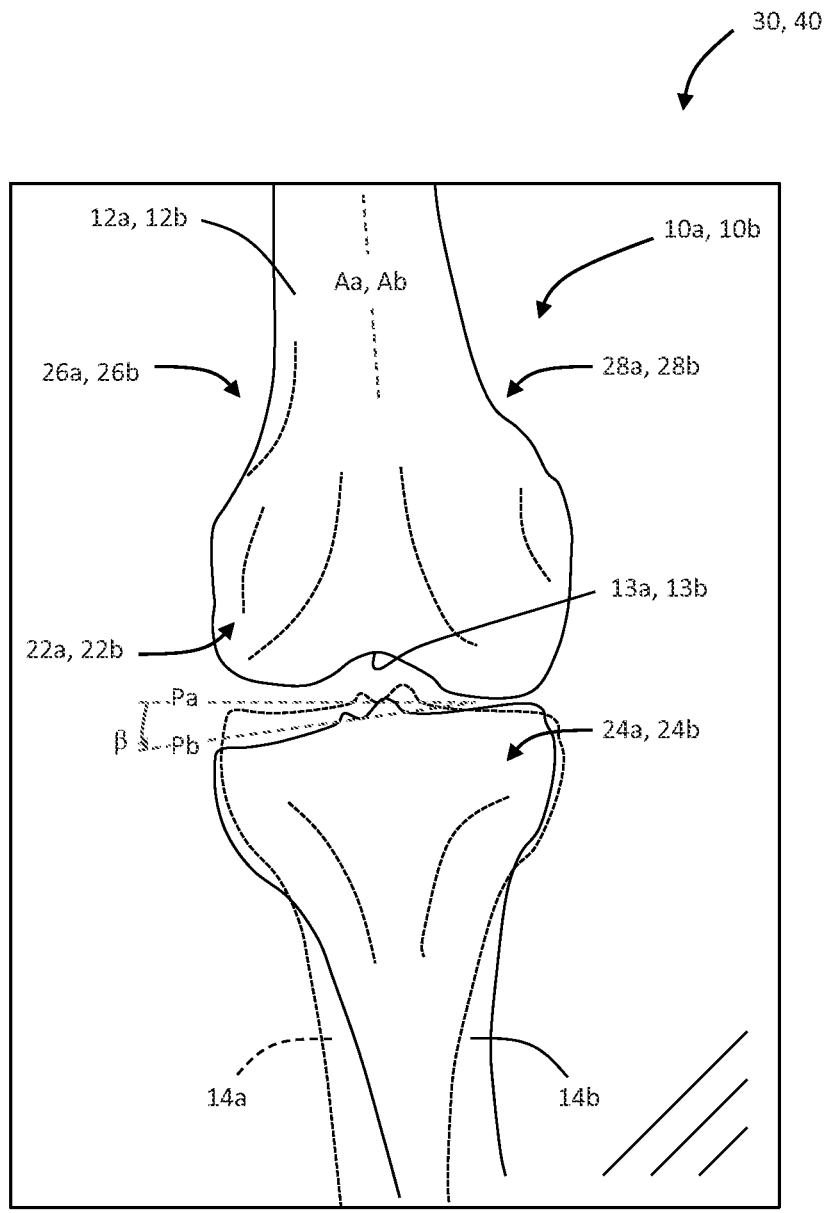
FIG. 6B is a plan view similar to FIG. 5 showing a second measurement of tibial movement between the first and second images.

As shown in FIG. 6B, the evaluating step 108 may also involve measuring an angle β between tibial plateau Pa of the first image 30 and tibial plateau Pb of the second image 40. Like angle α described above, angle β represents the degree of rotation between the patient's unloaded, supine knee joint 10a and the patient's loaded, standing knee joint 10b. Angle α may be the same as angle β.

Figure 6C:
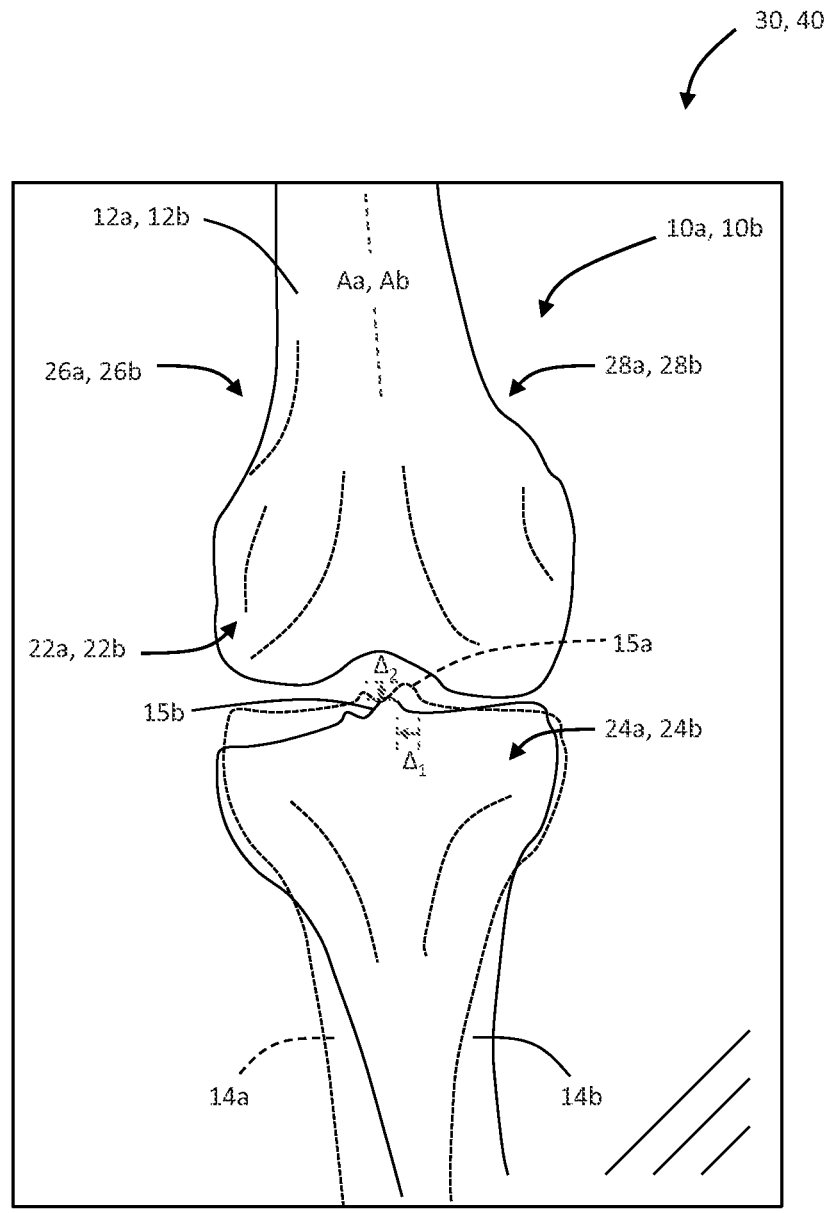
FIG. 6C is a plan view similar to FIG. 5 showing a third measurement of tibial movement between the first and second images.

As shown in FIG. 6C, the evaluating step 108 may also involve measuring a medial-lateral distance $\Delta_1$ between the tibial eminence 15a of the first image 30 and the tibial eminence 15b of the second image 40. In this embodiment, distance $\Delta_1$ represents a shift or translation between the patient's unloaded, supine knee joint 10a and the patient's loaded, standing knee joint 10b. In the illustrated embodiment of FIG. 6C, for example, the patient's knee joint becomes more varus when loaded, and in response, tibia 14b has shifted or translated laterally outward by distance $\Delta_1$ relative to femur 12b. In FIG. 6C, distance $\Delta_1$ is measured by comparing corresponding medial aspects or landmarks of tibial eminences 15a, 15b, but it is also within the scope of the present disclosure that distance $\Delta_1$ may be measured by comparing corresponding central aspects or landmarks or corresponding lateral aspects or landmarks of tibial eminences 15a, 15b, for example.

Referring still to FIG. 6C, the evaluating step 108 may further involve measuring a superior-inferior distance $\Delta_2$ between the tibial eminence 15a of the first image 30 and the tibial eminence 15b of the second image 40. In this embodiment, distance $\Delta_2$ represents a shift or translation between the patient's unloaded, supine knee joint 10a and the patient's loaded, standing knee joint 10b. In the illustrated embodiment of FIG. 6C, for example, tibia 14b has shifted or translated inferiorly by distance $\Delta_2$ relative to femur 12b. In FIG. 6C, distance $\Delta_2$ is measured by comparing corresponding medial aspects or landmarks of tibial eminences 15a, 15b, but like distance $\Delta_1$ discussed above, may be measured by comparing corresponding central aspects or landmarks or corresponding lateral aspects or landmarks of tibial eminences 15a, 15b, for example.

One skilled in the art may identify other variables similar to angle $\alpha$ (FIG. 6A), angle $\beta$ (FIG. 6B), and distances $\Delta_1$ and $\Delta_2$ (FIG. 6C) that may be used to evaluate differences between the first and second images 30, 40, including rotation variables. Such variables may be used in addition to or instead of angle $\alpha$, angle $\beta$, and distances $\Delta_1$ and $\Delta_2$ described herein.

Based on the evaluating step 108, the surgeon or another party determines the laxity or tension of the patient's knee joint 10 during step 110 of method 100 (FIG. 2). The more lax the surrounding soft tissue, the more knee joint 10 tends to move when loaded. Therefore, a relatively large angle $\alpha$ (FIG. 6A), a relatively large angle $\beta$ (FIG. 6B), a relatively large distance $\Delta_1$ (FIG. 6C), and/or a relatively large distance $\Delta_2$ (FIG. 6C) measured during step 108 may suggest that the patient's knee joint 10 is surrounded by lax soft tissue. By contrast, the more tense the surrounding soft tissue, the less knee joint 10 tends to move when loaded. Therefore, a relatively small angle $\alpha$ (FIG. 6A), a relatively small angle $\beta$ (FIG. 6B), a relatively large distance $\Delta_1$ (FIG. 6C), and/or a relatively small distance $\Delta_2$ (FIG. 6C) measured during step 108 may suggest that the patient's knee joint 10 is surrounded by tense soft tissue.

Based on the determining step 110, the surgeon or another party plans and surgically performs the knee arthroplasty procedure during step 112 of method 100 (FIG. 2). The knee arthroplasty procedure may involve resecting distal end 22 of the patient's femur 12 and/or proximal end 24 of the patient's tibia 14 and replacing the resected bones with prosthetic implants.

Figure 8:
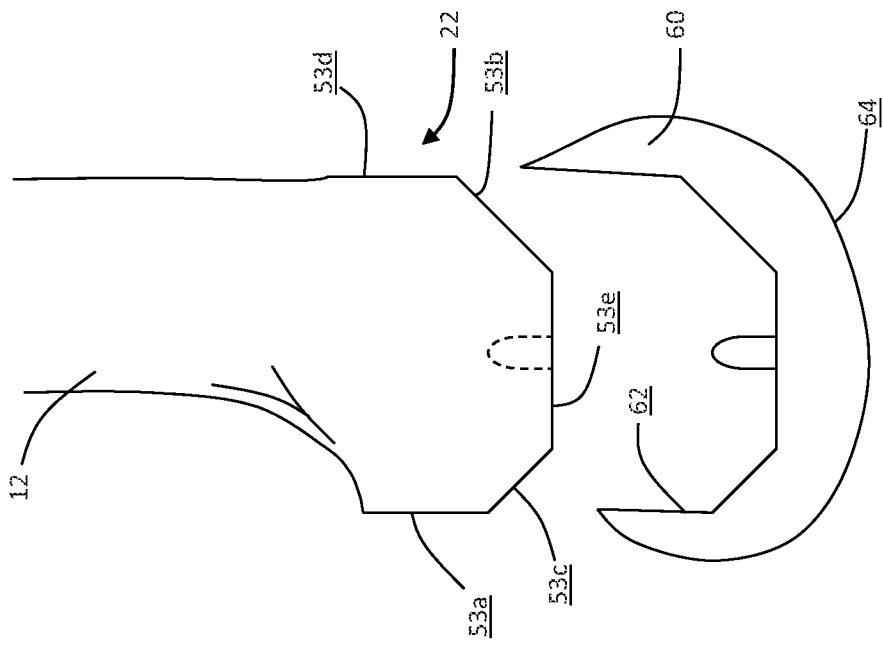
FIG. 8 is a side elevational view of the patient's resected femur shown with a corresponding femoral prosthesis.
Figure 7:
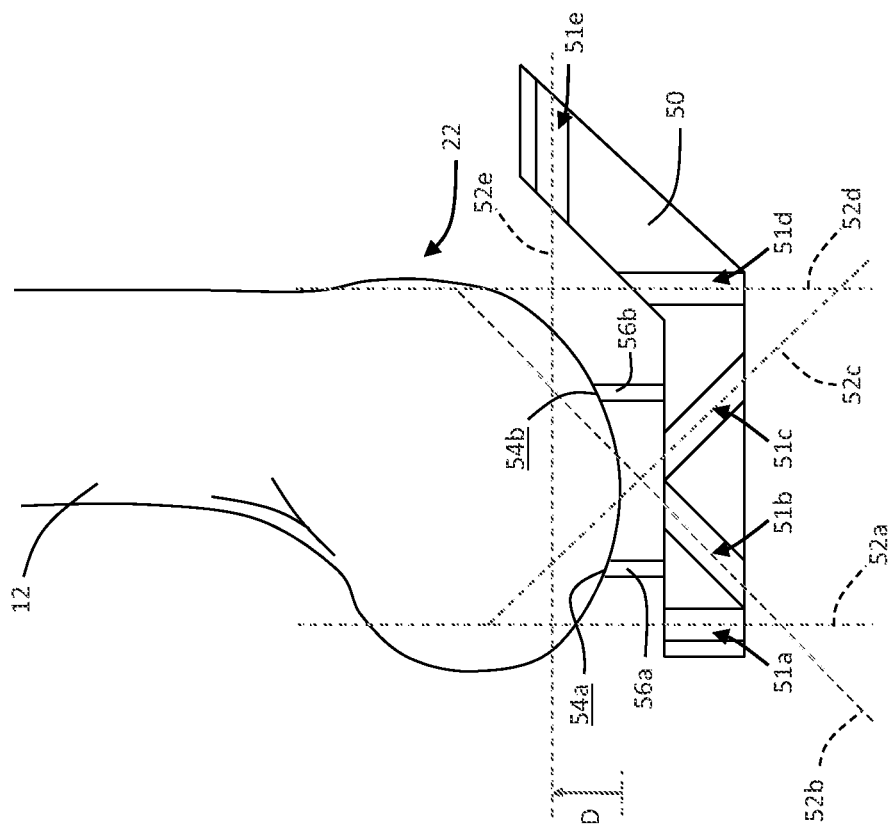
FIG. 7 is a side elevational view of the patient's femur shown with a cut guide for resecting the distal end of the patient's femur.

In FIG. 7, a cut guide 50 is shown for resecting distal end 22 of the patient's femur 12. Cut guide 50 includes at least one cut slot, illustratively cut slots 51a-51e, for guiding a cutting tool into the patient's femur 12 along corresponding cut planes 52a-52e to produce corresponding resected surfaces 53a-53e (FIG. 8). The cutting tool may include a saw blade or a mill, for example. Cut guide 50 further includes at least one abutting surface, illustratively abutting surfaces 54a, 54b of legs 56a, 56b, that abut the patient's femur 12. Cut guide 50 may be temporarily secured to the patient's femur 12 using mechanical fasteners or adhesive, for example.

According to an exemplary embodiment of the present disclosure, cut guide 50 is a patient-specific instrument, with the abutting surfaces 54a, 54b being shaped as substantially a negative of the particular patient's femur 12 so that cut guide 50 conforms to the particular patient's femur 12 and is perfectly contoured to fit against the particular patient's femur 12. Although the illustrative abutting surfaces 54a, 54b are located on spaced-apart legs 56a, 56b that contact discrete points on the distal end 22 of the patient's femur 12, it is also within the scope of the present disclosure that the abutting surfaces 54a, 54b may form a substantially continuous and concave surface that spans anteriorly and posteriorly to wrap around and contact at least a portion of distal end 22 of the patient's femur 12. In this manner, the continuous abutting surfaces would have more surface contact with the patient's femur 12 than the discrete abutting surfaces 54a, 54b shown in FIG. 7.

Cut guide 50 may be an entirely custom product that is manufactured using a casting/molding process or a rapid manufacturing process, such as 3-D printing, stereolithography, selective laser sintering, fused deposition modeling, laminated object manufacturing, or electron beam melting, for example. The custom cut guide 50 may be designed using a three-dimensional model of the patient's femur 12, which may include the above-described first image 30 (FIG. 3) of the patient's femur 12. Specifically, abutting surfaces 54a, 54b of the custom cut guide 50 may be designed to fit perfectly against the three-dimensional model of the patient's femur 12. In use, abutting surfaces 54a, 54b of the custom cut guide 50 will fit perfectly against the patient's actual femur 12. It is also within the scope of the present disclosure that cut guide 50 may be a partially custom product. For example, cut guide 50 may include a stock body with customizable, shapeable legs 56a, 56b.

Based on the shape of cut guide 50 and the length of legs 56a, 56b, for example, the patient's femur 12 is resected at depth D. In the illustrated embodiment of FIG. 7, the resection depth D is measured with respect to cut slot 51e and extends from the corresponding cut plane 52e to the distal-most end of the patient's femur 12. For most patient's, the distal-most end of femur 12 will lie on the medial femoral condyle (See, for example, the distally-located condyle on the medial side 28 of femur 12 in FIG. 1A), but it is also within the scope of the present disclosure that the distal-most end will lie on the lateral femoral condyle.

The resection depth D may be altered by customizing or adjusting cut guide 50. In one embodiment, the resection depth D may be altered by adjusting the length of legs 56a, 56b. For example, a stock cut guide 50 may be supplied having relatively long legs 56a, 56b, and then the stock cut guide 50 may be customized to arrive at a desired resection depth D by shortening and shaping legs 56a, 56b. In another embodiment, the resection depth D may be altered by adjusting the location of cut slots 51a-51e in cut guide 50 or by selecting another cut guide having different cut slot locations.

In FIG. 8, a corresponding femoral prosthesis 60 is shown for replacing the resected distal end 22 of the patient's femur 12. Femoral prosthesis 60 includes a bone-contacting surface 62 that is contoured to fit against resected surfaces 53a-53e of the patient's resected femur 12 and an opposing articulating surface 64 that is contoured to articulate with the patient's adjacent tibia 14 (FIG. 1A) or an adjacent tibial prosthesis 70 (FIG. 9).

Figure 9:
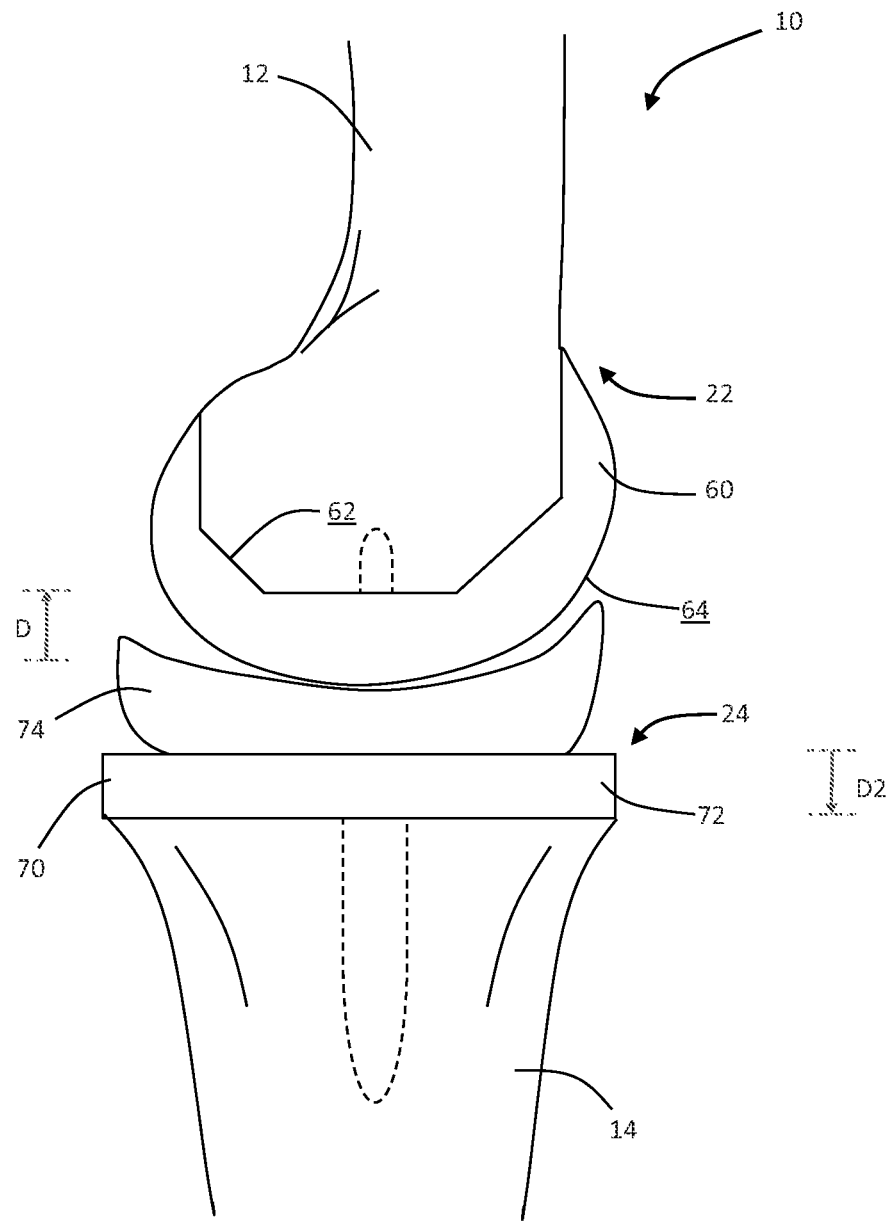
FIG. 9 is a side elevational view of the patient's surgically repaired knee joint, also including a tibial prosthesis that articulates with the femoral prosthesis.

In FIG. 9, tibial prosthesis 70 is shown for replacing the resected proximal end 24 of the patient's tibia 14. Tibial prosthesis 70 includes tray 72 that attaches to the patient's resected tibia 14 and a polymeric bearing layer 74 that is contoured to articulate with the adjacent femoral prosthesis 60. The polymeric bearing layer 74 may vary in thickness between about 10 mm and about 17 mm, for example.

If the resection depth D is too small, femoral prosthesis 60 would rest too shallow on the patient's femur 12 and too tight against tibial prosthesis 70. In particular, knee joint 10 may become tight when subjected to a load that forces femoral prosthesis 60 and tibial prosthesis 70 together. In this case, the freedom of movement between femoral prosthesis 60 and tibial prosthesis 70 could be too small. Also, the tight spacing between femoral prosthesis 60 and tibial prosthesis 70 may subject the patient's femur 12 and/or tibia 14 to greater forces than desired. To avoid this tight spacing, the surgeon may need to make intraoperative modifications, such as re-cutting the patient's femur 12, which increases the length of the surgical procedure.

If the resection depth D is too large, on the other hand, femoral prosthesis 60 would rest too deep into the patient's femur 12 and too loose relative to tibial prosthesis 70. In particular, knee joint 10 may become loose when not subjected to a load, allowing femoral prosthesis 60 and tibial prosthesis 70 to spread apart. In this case, the freedom of movement between femoral prosthesis 60 and tibial prosthesis 70 could be greater than desired. The loose spacing between femoral prosthesis 60 and tibial prosthesis 70 may cause the patient's knee joint 10 to function abnormally.

Method 100 of the present disclosure allows the surgeon to determine an appropriate resection depth D during pre-operative planning, thereby reducing intraoperative modifications. In an exemplary embodiment, the resection depth D chosen in accordance with method 100 is a patient-specific solution that is based on the laxity or tension of the particular patient's knee joint 10. From one patient to the next, method 100 enables the surgeon to achieve an appropriate freedom of movement between adjacent, articulating components, even as the soft tissue balance varies between patients.

As the evaluating step 108 indicates more tension in the surrounding soft tissue, the resection depth D increases by a proportional amount. A tense knee joint 10 may be recognized during step 108 as showing relatively little movement (e.g., a relatively small angle α (FIG. 6A), a relatively small angle β (FIG. 6B), a relatively large distance $\Delta_1$ (FIG. 6C), and/or a relatively small distance $\Delta_2$ (FIG. 6C)). Because the resection depth D increases as the movement measured during step 108 decreases, these variables are inversely proportional. As a result of increasing the resection depth D, and with reference to FIG. 9, femoral prosthesis 60 will be implanted deeper into femur 12 and further away from the tightly-held tibial prosthesis 70.

By contrast, as the evaluating step 108 indicates more laxity in the surrounding soft tissue, the resection depth D decreases by a proportional amount. A lax knee joint 10 may be recognized during step 108 as showing relatively large movement (e.g., a relatively large angle α (FIG. 6A), a relatively large angle β (FIG. 6B), a relatively large distance $\Delta_1$ (FIG. 6C), and/or a relatively large distance $\Delta_2$ (FIG. 6C)). Because the resection depth D decreases as the movement measured during step 108 increases, these variables are inversely proportional. As a result of decreasing the resection depth D, and with reference to FIG. 9, femoral prosthesis 60 will be implanted shallower into femur 12 and closer to the loosely-held tibial prosthesis 70.

In one embodiment, the surgeon adjusts an initial resection depth D by a desired amount. The initial resection depth D may be pre-selected based on accepted surgical practices, the average patient's needs, or the manufacturer's recommendations, for example. If femoral prosthesis 60 corresponds to an initial or planned resection depth D of about 20 millimeters (mm), for example, the surgeon may choose to increase the actual resection depth D above 20 mm (e.g., 21 mm, 22 mm, 23 mm, 24 mm, or more) to accommodate a tense knee joint 10, or the surgeon may choose to decrease the actual resection depth D below 20 mm (e.g., 19 mm, 18 mm, 17 mm, 16 mm, or less) to accommodate a lax knee joint 10.

In another embodiment, the surgeon selects resection depth D from a look-up table, such as Table 1 below. The table may include various angles α (FIG. 6A), angles β (FIG. 6B), distances $\Delta_1$ (FIG. 6C), and/or distances $\Delta_2$ (FIG. 6C) and corresponding resection depths D. The look-up table may include known patient data from previous procedures.

TABLE 1

| Sample Patient No. | Measured Angle β (°) | Measured Distance $\Delta_1$ (mm) | Resection Depth D (mm) |
| --- | --- | --- | --- |
| 1 | 6.9 | 8 | 20 (planned) − 4 |
| 2 | 2.64 | 1.4 | 20 (planned) + 0 |
| 3 | 8.1 | 3.2 | 20 (planned) − 2 |
| 4 | 3.2 | 2.1 | 20 (planned) + 0 |
| 5 | 7.1 | 4 | 20 (planned) − 2 |

In yet another embodiment, the surgeon calculates resection depth D as a function of angle α (FIG. 6A), angle β (FIG. 6B), and/or distance Δ (FIG. 6C).

Although the resection depth D is described herein with reference to the patient's femur 12, the same teachings may be applied to the patient's tibia 14. For example, as shown in FIG. 9, the more tense the surrounding soft tissue of knee joint 10, the greater the resection depth D2 may be into tibia 14, and the more lax the surrounding soft tissue of knee joint 10, the smaller the resection depth D2 may be into tibia 14. The resection depth D2 of tibia 14 may be adjusted instead of or in addition to the resection depth D of femur 12.

The above-described method 100 (FIG. 2) provides information to estimate the laxity or tension of knee joint 10. In addition to using this information to determine an appropriate resection depth D, as described above, the information may be used to generate a natural, dynamic simulation of the patient's knee joint 10 moving between flexion and extension, and vice versa, such as for surgical planning purposes. Additionally, this information may be used to predict flexion contractures.

While this invention has been described as having exemplary designs, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A method of performing an arthroplasty procedure on a patient's knee joint of a leg, the knee joint including a femur, a tibia, and soft tissue, the method comprising the steps of:

obtaining preoperatively a first image of the knee joint in an unloaded state and a second image of the knee joint in a loaded state, the unloaded state including no weight being applied to the tibia by the leg of the patient being laid down, and the loaded state including weight being applied to the tibia, the first image and the second image being at least one of MRI, CT and X-ray of the knee joint;

measuring preoperatively at least a distance between at least a first tibial anatomic feature and a first femoral anatomic feature of the knee joint in the first image;

measuring preoperatively at least a distance between at least the first tibial anatomic feature and the first femoral anatomic feature in the second image;

evaluating preoperatively a difference by comparing with image processing of a computer at least the measured distances of the first image and the second image, the difference being representative of laxity of the knee joint; and designing preoperatively a digital model of a patient-specific cut guide that is contoured three-dimensionally to fit against one of the femur and the tibia and configured to guide a cutting tool to a desired resection depth based on the laxity of the knee joint evaluated during the evaluating step, the patient-specific cut guide adapted to be used to resect at least one of the femur and the tibia with the cutting tool guided by the patient-specific cut guide and into one of the femur and the tibia.

2. The method of claim 1, further comprising capturing the first image of the knee joint, wherein the first image is captured with the patient lying down in the supine position.

3. The method of claim 1, further comprising capturing the second image of the knee joint, wherein the second image is captured with the patient standing.

4. The method of claim 1, wherein the measuring steps comprise measuring the first image as a three-dimensional model and measuring the second image as a two-dimensional image.

5. The method of claim 1, wherein the comparing step comprises overlapping corresponding regions of the femur in the first and second images.

6. The method of claim 5, wherein the overlapping is performed automatically by a computer by performing a best-fit calculation between the first and second images.

7. The method of claim 1, wherein said evaluating comprises evaluating a rotation of the tibia medially or laterally relative to the femur as the difference being representative of the laxity of the knee joint.

8. The method of claim 1, wherein said evaluating comprises evaluating a translation of the tibia medially or laterally relative to the femur as the difference being representative of the laxity of the knee joint.

9. The method of claim 1, wherein said designing comprises designing the patient-specific cut guide with the desired resection depth being inversely proportional to the difference evaluated during the evaluating.

10. The method of claim 1, wherein said obtaining comprises capturing the first image comprises taking one of a MRI and a CT of the knee joint.

11. The method of claim 1, wherein said obtaining comprises capturing the second image comprises taking an X-ray of the knee joint.

12. The method of claim 1, further comprising manufacturing the patient-specific cut guide.

13. The method of claim 1, further comprising digitally segmenting anatomic structures from the first image and the second image for measuring preoperatively said distance.

14. The method of claim 1, wherein obtaining preoperatively said first image and said second image comprises scaling at least one of said first image and said second image for anatomic features of the first image and the second image to be scaled to a same dimension.

15. The method of claim 14, wherein scaling at least one of said first image and said second image comprises capturing said first image and said second image with magnification markers.

* * * * *